US012369988B2

(12) United States Patent
Johnson et al.

(10) Patent No.: US 12,369,988 B2
(45) Date of Patent: Jul. 29, 2025

(54) TRACKER FOR A NAVIGATION SYSTEM

(71) Applicant: MAKO Surgical Corp., Ft. Lauderdale, FL (US)

(72) Inventors: Ezra Johnson, Reeds Spring, MO (US); William Daniel Weinlandt, Fort Lauderdale, FL (US); Jonathan Mark Morgan, Biscayne Park, FL (US); Larry Hazbun, Davie, FL (US)

(73) Assignee: MAKO Surgical Corp., Weston, FL (US)

(*) Notice: Subject to any disclaimer, the term of this patent is extended or adjusted under 35 U.S.C. 154(b) by 582 days.

(21) Appl. No.: 17/568,203

(22) Filed: Jan. 4, 2022

(65) Prior Publication Data
US 2022/0211441 A1  Jul. 7, 2022

Related U.S. Application Data

(60) Provisional application No. 63/134,283, filed on Jan. 6, 2021.

(51) Int. Cl.
*A61B 34/20* (2016.01)
*A61B 90/00* (2016.01)

(52) U.S. Cl.
CPC .............. *A61B 34/20* (2016.02); *A61B 90/39* (2016.02); *A61B 2034/2046* (2016.02)

(58) Field of Classification Search
CPC . A61B 34/20; A61B 90/39; A61B 2034/2046; A61B 34/30;
(Continued)

(56) References Cited

U.S. PATENT DOCUMENTS 3,790,912 A * 2/1974 Murphy ............. H01H 36/0006
362/310
4,777,582 A * 10/1988 Sharrah ..................... F21L 2/00
362/205
(Continued)

FOREIGN PATENT DOCUMENTS

CN  108784833 A  11/2018
DE  3312673 A1  10/1984
(Continued)

OTHER PUBLICATIONS

English language abstract and machine-assisted English translation for CN 108784833 A extracted from espacenet.com database on Jan. 20, 2022, 10 pages.
(Continued)

*Primary Examiner* — Bo Joseph Peng
(74) *Attorney, Agent, or Firm* — Howard & Howard Attorneys PLLC

(57) ABSTRACT

A tracker for a navigation system. A tracker body defines an opening, and a lens is positionable to seal the opening. A plug is configured to be coupled to the tracker body to secure the lens. A tracking element may be disposed between the lens and the plug so as to be visible through the lens. The tracking element may be disposed within a sealed enclosure defined by the lens and the plug. The plug may define a counterbore in fluid communication with the opening, and the plug may be at least partially disposed within the counterbore. The plug may further define a groove, and the tracker may include a sealing element disposed within the groove. The plug may include a shoulder configured to in sealing engagement with the tracker body. Methods of assembling the tracker for use with the navigation system are also disclosed.

8 Claims, 3 Drawing Sheets

(58) Field of Classification Search
CPC .. A61B 2017/00907; A61B 2034/2051; A61B 2034/2055; A61B 2090/0813; A61B 2090/3916; A61B 2090/3937; A61B 2090/397; A61B 2090/3983
See application file for complete search history.

(56) References Cited

U.S. PATENT DOCUMENTS

| | | | |
|---|---|---|---|
| 4,778,252 A | 10/1988 | Filho | |
| 4,807,097 A * | 2/1989 | Gammache | F21L 2/00 362/205 |
| 5,394,457 A | 2/1995 | Leibinger et al. | |
| 6,026,315 A | 2/2000 | Lenz et al. | |
| 6,298,262 B1 | 10/2001 | Franck et al. | |
| 6,333,971 B2 | 12/2001 | McCrory et al. | |
| 6,398,383 B1 * | 6/2002 | Huang | F21L 4/005 362/202 |
| 6,675,040 B1 | 1/2004 | Cosman | |
| 6,694,168 B2 | 2/2004 | Traxel et al. | |
| 6,856,828 B2 | 2/2005 | Cossette et al. | |
| 7,137,712 B2 | 11/2006 | Brunner et al. | |
| 7,461,945 B2 * | 12/2008 | Shiau | F21V 14/065 362/174 |
| 7,518,502 B2 | 4/2009 | Austin et al. | |
| 7,527,387 B2 | 5/2009 | Birkenbach | |
| 7,643,867 B2 | 1/2010 | Solar et al. | |
| 7,668,584 B2 | 2/2010 | Jansen | |
| 7,787,934 B2 | 8/2010 | Mazzocchi et al. | |
| 7,820,446 B2 | 10/2010 | Feilkas et al. | |
| 7,840,256 B2 | 11/2010 | Lakin et al. | |
| 7,874,686 B2 | 1/2011 | Rossner et al. | |
| 7,945,311 B2 | 5/2011 | McCloy et al. | |
| 8,073,530 B2 | 12/2011 | Solar et al. | |
| 8,172,434 B1 * | 5/2012 | Olsson | F21V 29/58 362/249.02 |
| 8,290,570 B2 | 10/2012 | Hoppe et al. | |
| 8,364,243 B2 | 1/2013 | Enzerink et al. | |
| 8,386,022 B2 * | 2/2013 | Jutras | A61B 34/20 600/407 |
| 8,412,308 B2 | 4/2013 | Goldbach | |
| 8,413,948 B2 | 4/2013 | Kemeny | |
| 8,416,403 B2 | 4/2013 | Nygaard | |
| 8,456,649 B2 | 6/2013 | Maier | |
| 8,534,848 B2 | 9/2013 | Hauri et al. | |
| 8,548,543 B2 | 10/2013 | Cinbis et al. | |
| 8,661,573 B2 | 3/2014 | Shafer et al. | |
| 8,662,683 B2 | 3/2014 | Rossner | |
| 8,668,340 B2 | 3/2014 | Jordanov et al. | |
| 8,668,345 B2 | 3/2014 | Shafer et al. | |
| 8,715,296 B2 | 5/2014 | Plassky et al. | |
| 8,727,565 B2 * | 5/2014 | Domagala | F21V 29/70 362/249.02 |
| 8,844,538 B2 | 9/2014 | Stang | |
| 8,864,326 B2 * | 10/2014 | Armer | F21L 4/00 362/249.02 |
| 8,915,599 B2 | 12/2014 | Rossner | |
| 9,044,269 B2 | 6/2015 | Woerlein | |
| 9,133,987 B2 * | 9/2015 | Domagala | F21V 7/041 |
| 9,226,686 B2 | 1/2016 | Blair | |
| 9,517,108 B2 | 12/2016 | Wildgruber et al. | |
| 9,574,760 B1 * | 2/2017 | Olsson | H05B 45/18 |
| 9,629,685 B2 | 4/2017 | Khoury | |
| 9,737,370 B2 | 8/2017 | Kheradpir et al. | |
| 9,746,170 B1 * | 8/2017 | Armer | F21V 29/58 |
| 9,808,321 B2 | 11/2017 | Huldin et al. | |
| 9,964,649 B2 | 5/2018 | Shafer et al. | |
| 10,034,713 B2 | 7/2018 | Yang et al. | |
| 10,070,940 B2 | 9/2018 | Bailey et al. | |
| 10,117,712 B2 | 11/2018 | Plassky et al. | |
| 10,335,239 B2 | 7/2019 | Plassky et al. | |
| 10,492,873 B2 | 12/2019 | Hallen et al. | |
| 10,751,137 B2 | 8/2020 | Zastrozna | |
| 10,939,977 B2 | 3/2021 | Messinger et al. | |
| 2001/0034530 A1 * | 10/2001 | Malackowski | A61B 34/20 606/130 |
| 2002/0149930 A1 * | 10/2002 | Parker | F21L 4/045 362/202 |
| 2004/0019265 A1 | 1/2004 | Mazzocchi et al. | |
| 2004/0030237 A1 | 2/2004 | Lee et al. | |
| 2004/0068263 A1 | 4/2004 | Chouinard et al. | |
| 2004/0116802 A1 | 6/2004 | Jessop et al. | |
| 2004/0188471 A1 * | 9/2004 | Cellini | F41H 9/10 222/192 |
| 2007/0093709 A1 | 4/2007 | Abernathie | |
| 2007/0100325 A1 * | 5/2007 | Jutras | A61B 90/39 606/1 |
| 2007/0167708 A1 | 7/2007 | Blumhofer et al. | |
| 2008/0287781 A1 | 11/2008 | Revie et al. | |
| 2008/0312530 A1 | 12/2008 | Malackowski et al. | |
| 2009/0275826 A1 | 11/2009 | Enzerink et al. | |
| 2010/0030231 A1 | 2/2010 | Revie et al. | |
| 2010/0076306 A1 | 3/2010 | Daigneault et al. | |
| 2012/0016427 A1 * | 1/2012 | Stindel | A61B 17/8023 606/86 R |
| 2013/0006120 A1 | 1/2013 | Druse et al. | |
| 2014/0261456 A1 * | 9/2014 | Malackowski | A61B 34/20 128/849 |
| 2015/0018672 A1 | 1/2015 | Blumhofer et al. | |
| 2015/0209119 A1 | 7/2015 | Theodore et al. | |
| 2015/0282735 A1 | 10/2015 | Rossner | |
| 2015/0351863 A1 | 12/2015 | Plassky et al. | |
| 2015/0359456 A1 | 12/2015 | Urban et al. | |
| 2016/0135904 A1 | 5/2016 | Daon et al. | |
| 2016/0175064 A1 | 6/2016 | Steinle et al. | |
| 2016/0228033 A1 | 8/2016 | Rossner | |
| 2016/0235480 A1 * | 8/2016 | Scholl | A61B 34/10 |
| 2016/0345917 A1 | 12/2016 | Daon et al. | |
| 2017/0007353 A1 | 1/2017 | Fleig et al. | |
| 2017/0020622 A1 | 1/2017 | Huldin et al. | |
| 2017/0042635 A1 | 2/2017 | Wildgruber et al. | |
| 2017/0071677 A1 | 3/2017 | Utz et al. | |
| 2017/0086941 A1 | 3/2017 | Marti et al. | |
| 2017/0165005 A1 | 6/2017 | Kheradpir et al. | |
| 2017/0165006 A1 * | 6/2017 | Woods | A61B 90/39 |
| 2017/0231715 A1 | 8/2017 | Roger et al. | |
| 2017/0238998 A1 | 8/2017 | Srimohanarajah et al. | |
| 2017/0239015 A1 | 8/2017 | Sela et al. | |
| 2017/0252109 A1 | 9/2017 | Yang et al. | |
| 2017/0281283 A1 | 10/2017 | Siegler et al. | |
| 2017/0281300 A1 | 10/2017 | Malackowski et al. | |
| 2018/0071029 A1 | 3/2018 | Srimohanarajah et al. | |
| 2018/0078332 A1 | 3/2018 | Mozes et al. | |
| 2018/0116746 A1 | 5/2018 | Lennertz et al. | |
| 2018/0185113 A1 | 7/2018 | Gregerson et al. | |
| 2018/0199999 A1 | 7/2018 | Syverson et al. | |
| 2018/0221108 A1 | 8/2018 | Broers et al. | |
| 2018/0271511 A1 | 9/2018 | Stanton | |
| 2018/0338799 A1 | 11/2018 | Hladio et al. | |
| 2020/0155241 A1 | 5/2020 | Cascarano et al. | |
| 2020/0305986 A1 | 10/2020 | Hladio et al. | |

FOREIGN PATENT DOCUMENTS

| | | |
|---|---|---|
| DE | 202004011567 U1 | 11/2004 |
| DE | 10331885 A1 | 2/2005 |
| DE | 102007055456 A1 | 5/2009 |
| DE | 202015106804 U1 | 1/2016 |
| EP | 1057589 A1 | 12/2000 |
| EP | 1639958 A1 | 3/2006 |
| EP | 2390068 A1 | 11/2011 |
| EP | 2124801 B1 | 5/2014 |
| WO | 9938449 A1 | 8/1999 |
| WO | 2001026574 A1 | 4/2001 |
| WO | 2003020146 A2 | 3/2003 |
| WO | 2003020146 A3 | 4/2003 |
| WO | 2009134367 A1 | 11/2009 |
| WO | 2010055193 A1 | 5/2010 |
| WO | 2012013304 A1 | 2/2012 |
| WO | 2012045626 A1 | 4/2012 |
| WO | 2015058816 A1 | 4/2015 |

(56) References Cited

FOREIGN PATENT DOCUMENTS

| WO | 2016044934 A1 | 3/2016 |
|---|---|---|
| WO | 2019245369 A1 | 12/2019 |
| WO | 2020072335 A1 | 4/2020 |

OTHER PUBLICATIONS

English language abstract and machine-assisted English translation for DE 3312 673 A1 extracted from espacenet.com database on Jan. 20, 2022, 5 pages.

English language abstract and machine-assisted English translation for DE 20 2004 011 567 U1 extracted from espacenet.com database on Jan. 20, 2022, 12 pages.

English language abstract and machine-assisted English translation for DE 10 331 885 A1 extracted from espacenet.com database on Jan. 20, 2022, 6 pages.

English language abstract and machine-assisted English translation for DE 10 2007 055 456 A1 extracted from espacenet.com database on Jan. 20, 2022, 21 pages.

Machine-assisted English language abstract and machine-assisted English translation for DE 20 2015 106 804 U1 extracted from espacenet.com database on Jan. 20, 2022, 18 pages.

English language abstract and machine-assisted English translation for EP 1 057 589 A1 extracted from espacenet.com database on Jan. 20, 2022, 8 pages.

English language abstract and machine-assisted English translation for EP 1 639 958 A1 extracted from espacenet.com database on Jan. 20, 2022, 13 pages.

English language abstract and machine-assisted English translation for EP 2 390 068 A1 extracted from espacenet.com database on Jan. 20, 2022, 9 pages.

English language abstract of EP 2 124 801 B1 and machine-assisted English translation for corresponding WO 2008/104548 A1 extracted from espacenet.com database on Jan. 20, 2022, 11 pages.

English language abstract and machine-assisted English translation for WO 2001/026574 A1 extracted from espacenet.com database on Jan. 20, 2022, 8 pages.

English language abstract and machine-assisted English translation for WO 03/020146 A2 extracted from espacenet.com database on Jan. 20, 2022, 7 pages.

English language abstract and machine-assisted English translation for WO2012013304 A1 extracted from espacenet.com database on Jan. 20, 2022, 9 pages.

International Search Report for Application No. PCT/US2022/011089 dated Apr. 29, 2022, 2 pages.

\* cited by examiner

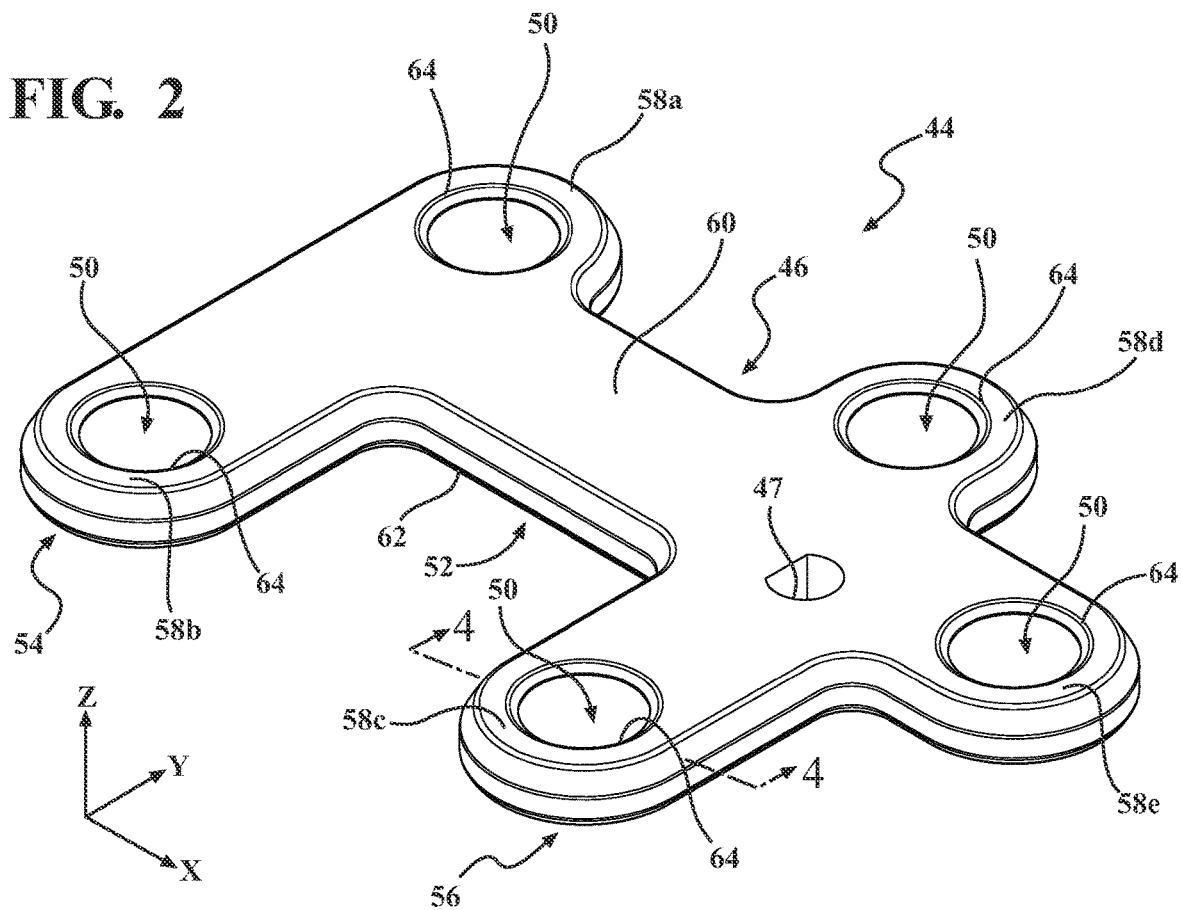
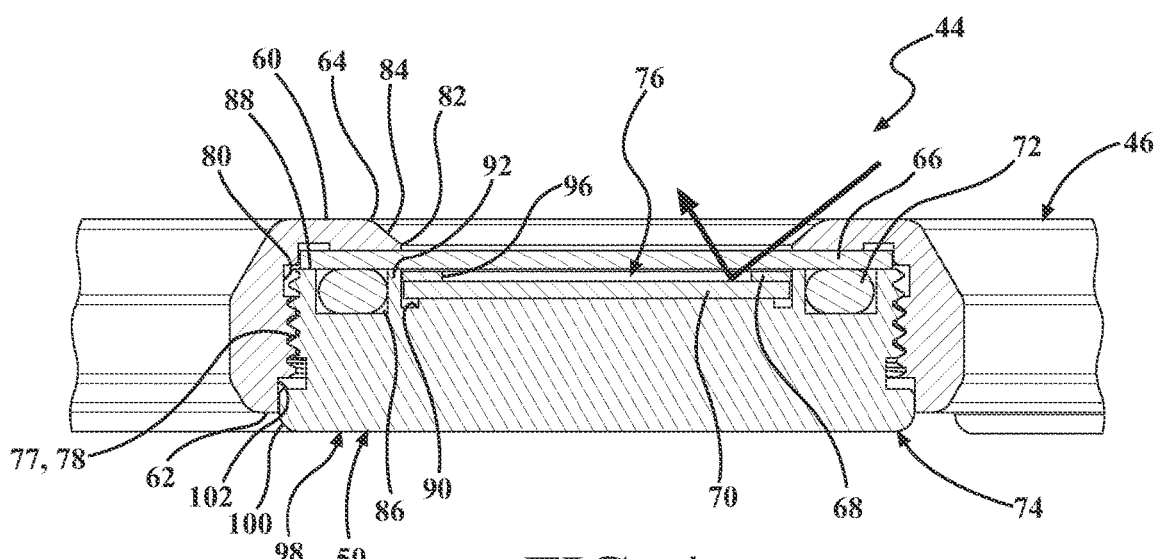

TRACKER FOR A NAVIGATION SYSTEM

CROSS-REFERENCE TO RELATED APPLICATIONS

The subject application claims priority to and all the benefits of U.S. Provisional Patent App. No. 63/134,283, filed Jan. 6, 2021, the contents of which are hereby incorporated by reference in its entirety.

BACKGROUND

Surgical navigation systems assist users with locating objects in the surgical field. More particularly, optical navigation systems may employ light signals in order to track the position and orientation of the objects such as surgical instrumentation and patient anatomy. A localizer may cooperate with tracking elements on a tracker to determine the position and orientation of the objects. The tracking elements may be passive elements so as to reflect light, or active elements so as to emit the light itself. Other navigation systems may utilize electromagnetic or radiofrequency wavelengths. The tracker may be mounted to the surgical instrumentation with a suitable coupler, or to the patient anatomy with a suitable fastener. For example, a bone plate may be provided to secured to bony anatomy, after which the tracker is coupled to the bone plate with an arm or post.

The surgical field should be sterile, and surgical instrumentation that is reusable should be sterilized between surgical procedures. This is typically accomplished through autoclaving in which the instrumentation is subjected to pressurized steam for a duration. Owing to the materials forming the tracking elements, passive tracking elements are not well suited to endure repeated autoclaving without compromise of their light-reflecting qualities. For example, the passive tracking elements may include a reflective film that may deteriorate when repeatedly exposed to the pressurized steam. It is known to replace the tracking elements after each surgical procedure; however, doing so is cumbersome and associated with added expense.

Therefore, a need exists in the art for a tracker designed to overcome one or more of the aforementioned disadvantages.

SUMMARY

This Summary introduces a selection of concepts in a simplified form that are further described in the Detailed Description below. This Summary is not intended to limit the scope of the claimed subject matter and does not necessarily identify each and every key or essential feature of the claimed subject matter.

According to a first aspect, a tracker for a navigation system is provided. The tracker includes a tracker body that defines an opening extending through the tracker body, a lens and a tracking element positionable in the opening, and a plug to seal the opening at a first end, position the tracking element within the opening, and support the lens within the opening to seal the opening at a second end with the lens.

According to a second aspect, a tracker for a navigation system is provided. The tracker comprises: a tracker body defining a counterbore; a lens positionable within the counterbore; a plug comprising a plug body at least partially positionable within the counterbore; and a tracking element disposed between the lens and the plug body; wherein the plug is configured to be coupled with the tracker body to secure the lens and to define, with the lens, a sealed enclosure, wherein the tracking element is disposed within the sealed enclosure.

According to a third aspect, a tracker for a navigation system is provided. The tracker comprises: a tracker body having an upper surface and a lower surface opposite the upper surface, the tracker body defining an opening extending between the upper surface and the lower surface, and a lip surrounding the opening, and a complementary retention feature disposed between the upper surface and the lower surface; a lens configured to abut the lip; and a plug comprising a plug body, and a retention feature coupled to the plug body and configured to be removably coupled with the complementary retention feature of the tracker body, and wherein the plug is configured to support a tracking element, maintain abutment between the lens and the lip to provide a first seal for opening near the upper surface, and maintain abutment between the plug body and the tracker body to provide a second seal near the lower surface.

According to a fourth aspect, a tracker for a navigation system is provided. The tracker comprises: a tracker body defining an opening; a lens positionable to seal the opening; a tracking element; a sealing element configured to be compressed against the lens; and a plug comprising a plug body comprising an upper surface defining a groove and further defining a cavity separate from the groove, wherein the sealing element is configured to be disposed within the groove and the tracking element is configured to be disposed within the cavity.

According to a fifth aspect a navigation system includes the tracker according to any of the above aspects, and optionally, any of their corresponding implementations. The navigation system may include includes a camera include optical sensors configured to detect light reflected by the tracking element.

According to a sixth aspect, a method of assembling a tracker for use with a navigation system is disclosed. A sealing element is disposed within a groove defined by a plug. A tracking element is disposed within a cavity defined by the plug. A masking spacer may be positioned within the cavity and to rest upon the tracking element. The lens may be positioned to rest upon the sealing element. The plug may be coupled to the tracker body. For example, the tracking element assembly, which includes the lens, the masking spacer, the tracking element, the sealing element, and the plug, may be rotated relative to the tracker body to engage complementary threads. In certain implementations, the tracker body defines an opening and a counterbore separated by a lip. The plug may be at least partially positioned within the counterbore. The sealing element may be compressed against the lens with abutment between the lens and the lip sealing the opening.

Any of the aspects may be combined in part, or in whole. Any of the aspects may be utilized, in part, or in whole, with any of the following implementations.

In certain implementations, the tracker, when assembled, is configured to prevent the tracking element from being exposed to fluid, for example, pressurized steam during autoclaving. The tracking element assembly includes a lens, the tracking element, and a plug configured to be coupled to the tracker body. The coupling may be a removable coupling, or a permanent joining. The tracking element may be a passive element or an active element. Preventing exposure of the tracking element to the fluid may eliminate the need to separately sterilize the tracking element, thereby extending the operational lifespan of the tracking element. In some implementations, the tracker is specifically a surgical navigation tracker to be attached to a surgical object, such as a patient, a tool, a robotic manipulator, a surgical table, an imaging device, a hand-held tool, a hand-held scanner or imager, or the like.

In certain implementations, the lens may be transparent, and tracking element may be disposed between the lens and the plug body so as to be visible through the lens. The tracker body may define an opening, and a counterbore in fluid communication with the opening. The plug body may be at least partially positionable within the counterbore. The plug, when coupled to the tracker body, secures the lens in place. The lens and the plug define a sealed enclosure within which the tracking element is disposed.

In certain implementations, an upper surface of the lens is transparent, and a lower surface of the lens includes a reflective coating to define the tracking element. In other words, a back of the lens may include the tracking element. The lens and/or the tracker body may otherwise include an anti-reflective coating. Alternatively, an upper surface of the plug may include a reflective coating to define the tracking element. The tracker body may include a lip separating the opening and the counterbore. The tracker body may include an upper surface including the lip and defining the opening, and an opposite lower surface defining the counterbore. The lip may include a chamfer extending inwardly away from an upper surface of the tracker body. The plug may support the lens in abutment with the lip to seal the counterbore. The counterbore may be circular, rectangular or any other constant or varying cross-sectional shape.

In certain implementations, the plug includes a shoulder extending radially outwardly from the plug body. The shoulder is positionable in sealing engagement with a widened portion of the counterbore. The plug body may further define a cavity, and the tracking element may be disposed within the cavity. A masking spacer may be disposed within the cavity and between the lens and the tracking element. The plug body may further define a groove. A sealing element may be disposed within the groove. The sealing element may include a thickness greater than a depth of the groove so as to be compressed against the lens. The cavity and the groove may be coaxially arranged.

In certain implementations, the tracker body includes a retention feature configured to be removably coupled with a complementary retention feature of the plug. The retention feature may be between the upper and lower surfaces of the tracker body, for example, be internal threads disposed within the counterbore. Engagement of the retention features may maintain abutment between the lens and the lip to seal the opening, and further maintain abutment between the plug body and the tracker body to provide another seal at the lower surface. The lens and the plug may be disposable within the counterbore from the lower surface.

In certain implementations, the tracker body further comprises a central portion, and an end portion wider than the central portion and including a flange. The flange may define the opening through which the tracking element is visible. There may be more than one flange, for example, three or more flanges. For example, the tracking body may include five flanges. The five flanges may be arranged between two end portions separated by the central portion in a generally pentagonal configuration. The tracker body may be plate-like in construction such that the tracking element assemblies are coplanar. Alternatively, the tracking element assemblies may be positioned and oriented in three-dimensions. The tracking element may be planar (e.g., discs), as shown, or hemispherical, spherical, or any other suitable geometry. The tracking element may be a passive element or an active element.

In certain implementations, the lens may be transparent, translucent, or have any characteristic of light admittance. The tracking element, the lens and/or the plug may include a reflective coating. A discrete component constituting the tracking element may be eliminated with the coating being on the lens and/or the plug. The coating forming the tracking element is positioned between the upper surface of the lens and the plug body. In other words, the tracking element may be embedded on or between the lens and the plug. The tracking element is disposed within the sealed enclosure. In an alternative implementation, the lens may be opaque to light but transmissive to electromagnetic (EM) or radiofrequency (RF) wavelengths. The tracking element may be configured to reflect the EM or RF waves. For example, the tracking element may be an EM or RF disc, strip, or element.

BRIEF DESCRIPTION OF THE DRAWINGS

Advantages of the present disclosure will be readily appreciated as the same becomes better understood by reference to the following detailed description when considered in connection with the accompanying drawings.

FIG. 2 is a perspective view of a tracker, according to one implementation.

FIG. 4 is a sectional view of the tracker of FIG. 3 taken along section lines 4-4.

DETAILED DESCRIPTION

Figure 1:
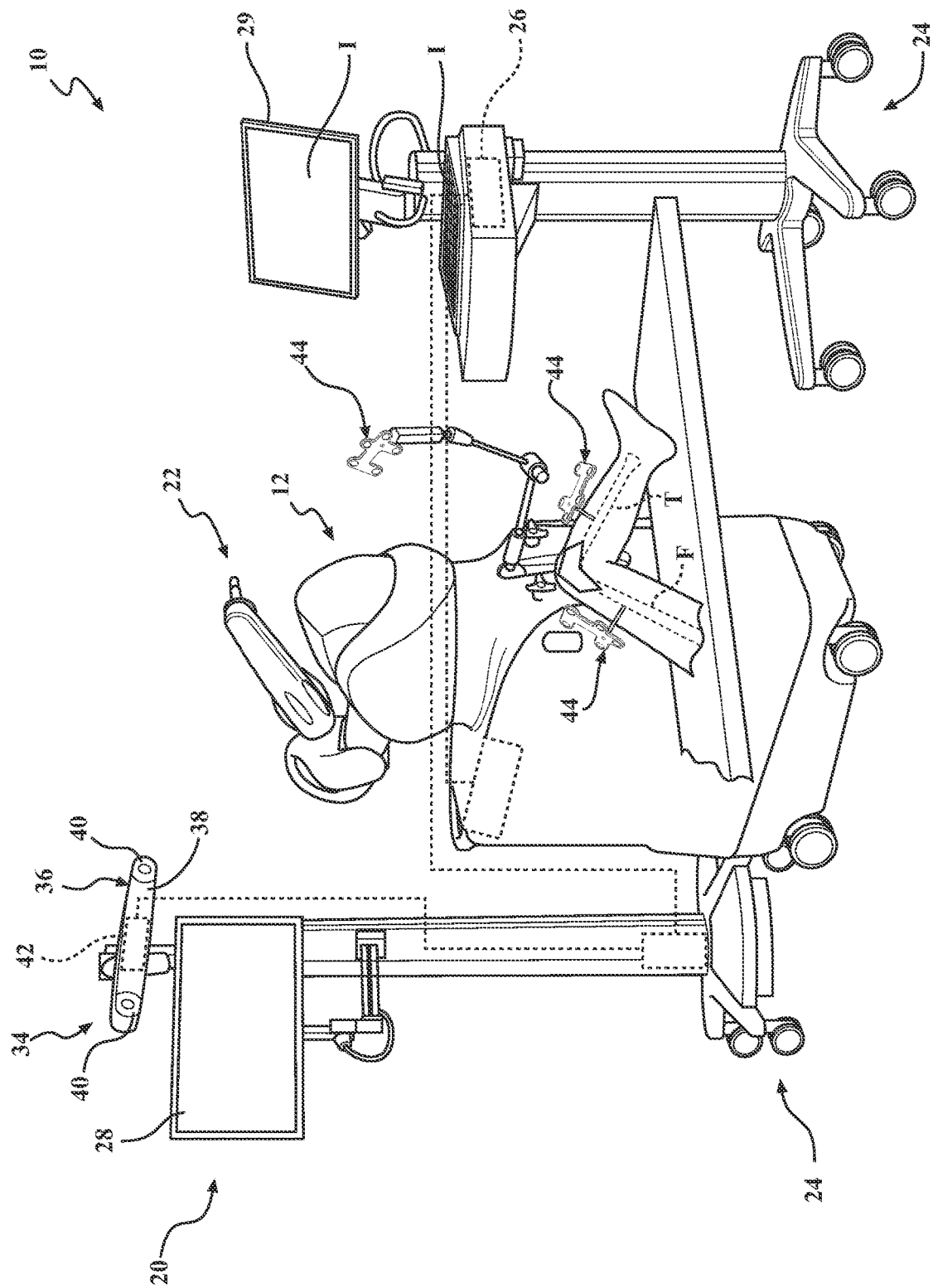
FIG. 1 is a perspective view of one implementation of a surgical system.

FIG. 1 illustrates an example of a surgical robotic system 10 for treating a patient. The robotic system 10 is shown in a surgical setting such as an operating room of a medical facility. In the embodiment shown, the robotic system 10 includes a manipulator 12 and a navigation system 20. The navigation system 20 is arranged to track movement of various real objects in the operating room. Such real objects include, for example, a surgical tool 22, a femur F of a patient, and a tibia T of the patient. The navigation system 20 tracks these objects for purposes of displaying their relative positions and orientations to the surgeon and, in some cases, for purposes of controlling or constraining movement of the surgical tool 22 relative to virtual cutting boundaries (not shown) associated with the femur F and tibia T.

The navigation system 20 includes one or more computer cart assemblies 24 that houses one or more navigation controllers 26. A navigation interface is in operative communication with the navigation controller 26. The navigation interface includes one or more displays 28, 29 adjustably mounted to the computer cart assembly 24 or mounted to separate carts as shown. Input devices I such as a keyboard and mouse can be used to input information into the navigation controller 26 or otherwise select/control certain aspects of the navigation controller 26. Other input devices I are contemplated including a touch screen, voice-activation, gesture sensors, and the like.

A surgical navigation localizer 34 communicates with the navigation controller 26. In the embodiment shown, the localizer 34 is an optical localizer and includes a camera unit 36. The camera unit 36 has a housing 38 comprising an outer casing that houses one or more sensors 40. In some implementations at least two sensors 40 are employed, and preferably three or four. The sensors 40 may be separate charge-coupled devices (CCD). For example, three, one-dimensional CCDs may be employed. Alternatively, two-dimensional or three-dimensional sensors may be provided. The CCDs detect light signals, such as infrared (IR) signals. In alternative implementations, the localizer 34 may be an EM or RF localizer configured to emit EM and RF waves, respectively, and the camera unit 36 is configured to detect EM or RF signals.

The camera unit 36 may be mounted on an adjustable arm to position the sensors 40 with a field-of-view of the below discussed trackers that, ideally, is free from obstructions. The camera unit 36 includes a camera controller 42 in communication with the sensors 40 to receive signals from the sensors 40. The camera controller 42 communicates with the navigation controller 26 through either a wired or wireless connection (not shown). Position and orientation signals and/or data are transmitted to the navigation controller 26 for purposes of tracking objects. The navigation controller 26 is loaded with software that converts the signals received from the camera unit 36 into data representative of the position and orientation of the objects being tracked.

The navigation system 20 is operable with a plurality of tracking devices 44, also referred to herein as trackers. In the illustrated implementation, one of the trackers 44 is firmly affixed to the femur F of the patient, and another one of the trackers 44 is firmly affixed to the tibia T of the patient. Additionally, or alternatively, still another tracker 44 may be mounted to other tissue types or parts of the anatomy. The tracker 44 of the present disclosure to be described is particularly well suited for applications involving delicate anatomy in which the weight of the tracker 44 be minimized, such as surgery of the shoulder, the spine, or the like. An additional tracker 44 may be also be coupled to the manipulator 12, as shown in FIG. 1. It is further contemplated that the tracker 44 may be coupled to any suitable surgical instrumentation, for example, a surgical power tool or a point probe for calibration or any non-powered tool. The tracker 44 may be utilized with the robotic system 10 or any other robotic surgical system, including hand-held robotic systems, table mounted robotic systems, etc. Additionally, or alternatively, the tracker 44 can be utilized by the navigation system without robotics to track other objects, such as imaging systems (e.g., CT, MRI, X-ray, etc.), soft tissue retractors, implants, the surgical table, cut guides, head-mounted devices, surgical drapes, mobile display devices (e.g., tablets), the practitioner or staff within the sterile field, and the like.

The sensors 40 of the localizer 34 receive light signals from the tracker(s) 44. In implementations in which the tracker 44 is a passive tracker, light emitted from the camera unit 36 is reflected by the tracker 44. Additionally, or alternatively, the tracker 44 may be an active tracker in which, for example, light emitting diodes (LEDs) transmit light. The camera unit 36 receives optical signals from the tracker(s) 44 and outputs to the navigation controller 26 signals relating to the position of the tracking elements of the tracker(s) 44 relative to the localizer 34. Based on the received optical signals, the navigation controller 26 generates data indicating the relative positions and orientations of the tracker(s) 44 relative to the localizer 34.

Referring now to FIG. 2, the tracker 44 includes a tracker body 46 that may define the form factor or shape of the tracker 44. The tracker body 46 may be of unitary of monolithic construction, as illustrated, or of subcomponents joined to one another. The tracker body 46 may be formed from any suitable material, such as steel or rigid plastic (e.g., thermoplastic polymer). In one example, the material is polyethylene terephthalate glycol. The material should be able to withstand pressures and temperatures associated with autoclaving. In an exemplary implementation, the tracker body 46 may be formed from a light plastic so as to minimize the overall weight of the tracker 44, which, as mentioned, may facilitate its use with more delicate anatomy. More specifically, whereas the femur F, the tibia T, other long bones, the iliac crest, and the like may be sufficiently large to accommodate a larger fastener so as to support a heavier tracker, less robust anatomy such as the patella, vertebrae, bones of the foot, and the like may be better served with a smaller fastener and lighter tracker. The tracker 44 of the present disclosure advantageously realizes that benefit.

The tracker body 46 may comprise an anti-reflecting light material. In another example, the tracker body 46 may comprise features formed in or disposed the body 46 that are designed to reduce light reflection. Such features may include surface roughness (e.g., Rz in the range of 14-18), dimples or indentations, or an anti-reflective paint or material disposed or formed on/within the tacker body 46. The tracker body 46 can be opaque, translucent or transparent to light. In implementations where the tracker body 46 is transparent, the tracker body 46 itself may form the lens with no discrete lens being further necessitated.

The tracker body 46 may define a coupler opening 47 configured to be removably coupled with an arm or post mounted to the object being tracked. An underside of the tracker body 46 may further define recesses configured to interface with the arm or post for confidently securing the tracker 44 to the object being tracked.

The form factor of the tracker body 46 may assume any suitable geometry so as to arrange a plurality of tracking element assemblies 50 in a desired spatial relationship. FIG. 2 shows one example of the tracker body 46 including a central portion 52 that is elongate with a length greater than a width, a first end portion 54 having a width greater than the width of the central portion 52, and a second end portion 56 also having a width greater than the width of the central portion 52. The respective widths of the first end portion 54 and the second end portion 56 may be defined between flanges 58a-58e (collectively identified herein as 58) sized to accommodate the tracking element assemblies 50. The illustrated implementation shows the first end portion 54 including two flanges 58a, 58b, and the second end portion 56 including three flanges 58c, 58d, 58e. The two flanges 58a, 58b are positioned opposite the central portion 52, and the three flanges 58c, 58d, 58e are in a generally cruciform configuration. The resulting arrangement includes five of the flanges 58a-58e to which five of the tracking element assemblies 50 are coupled in a pentagonal configuration. Of course, fewer or more of the tracking element assemblies 50 are contemplated for which there could be fewer or more flanges 58. For the central portion 52 is optional, wherein the first end portion 54 or the second end portion 56 is absent. The size of the flanges 58a-58e and their relative positioning relative to one another may be sufficient spaced apart for the sensors 40 to discretely detect the light signals from each of the tracking element assemblies 50. It is further contemplated that the tracking element assemblies 50 may be coupled to the central portion 52 as well.

The tracking element assemblies 50 may be in a coplanar arrangement. The illustrated implementation shows the tracker body 46 being plate-like in construction with a relatively small thickness defined between an upper surface 60 opposite a lower surface 62. The upper surface 60 may define openings 64 through which a respective one of the tracking element assemblies 50 is configured to be visible by the sensors 40. With the tracking element assemblies 50 coupled to the tracker body 46 as illustrated in FIG. 2, the tracking element assemblies 50 are spaced apart from one another in two directions (x and y), but otherwise coplanar in the z-direction. In alternative implementations, the tracker body 46 may include geometric features in the z-direction, and the tracking element assemblies 50 may be suitably positioned and oriented in three dimensions relative to one another. The tracker 44 may include any number of tracking element assemblies 50, and these assemblies need not necessarily be disposed in flanges 58 as specifically shown. One skilled in the art could construct the tracker body 46 to be any number of shapes wherein the tracking element assemblies 50 can remain readily visible.

Figure 3:
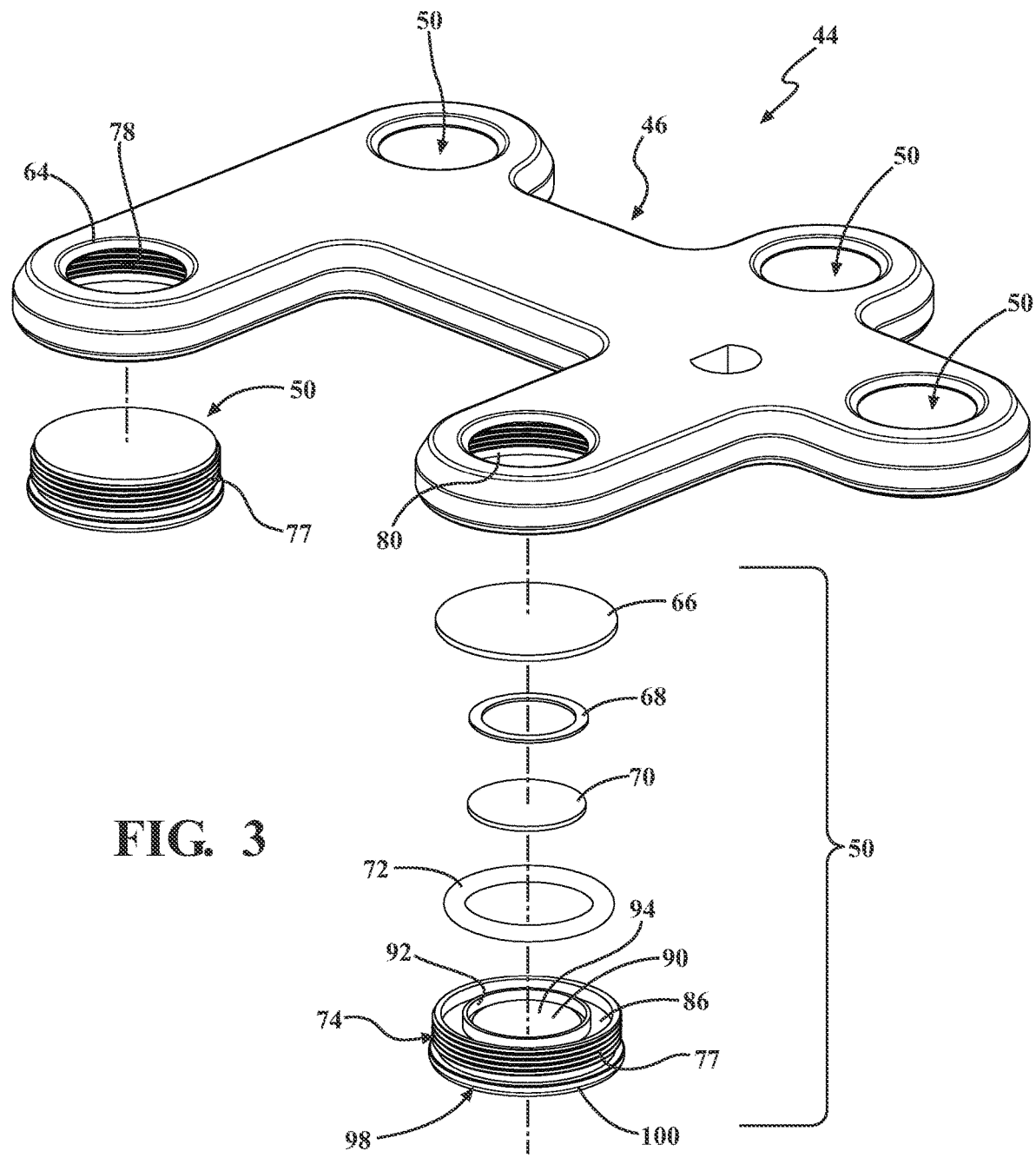
FIG. 3 is an exploded view of the tracker, according to one implementation.

With concurrent reference to FIGS. 3 and 4, the tracker 44 includes the tracking element assemblies 50 configured to be coupled to the tracker body 46. One of the tracking element assemblies 50 is to be further discussed in detail with the disclosure applicable to any number of the tracking element assemblies 50 provided on the tracker 44. The tracking element assembly 50 may include a lens 66, a masking spacer 68, a tracking element 70, a sealing element 72, and a plug 74. When installed to the tracker body 46, subcomponents of the tracking element assembly 50 define a sealed enclosure 76 for the tracking element 70. The sealed enclosure 76 advantageously prevents the tracking element 70 from being exposed to gas and fluid, for example, pressurized steam associated with autoclaving. Therefore, the tracker 44 may be repeatedly autoclaved as a single unit without need to decouple the tracking element assembly 50, and further without the need to replace the tracking element 70 after each use or few uses. Relative to known trackers, the tracker 44 of the present disclosure provides for a longer operational lifespan with less maintenance and less expense. Empirical data shows the tracker 44 may be confidently sterilized and reused for at least two-hundred duty cycles without degradation of the sealed enclosure 76 (and thus preservation of the wavelength-reflecting equalities of the tracking element 70).

As appreciated from the exploded aspects of FIG. 3, the tracking element assembly 50 includes a coaxial stacking of the subcomponents in a specific arrangement to achieve the sealed enclosure 76. Further the specific arrangement of the subcomponents provides for simplified construction and intuitive coupling and decoupling of the tracking element assembly 50 and the tracker body 46. More particularly, the plug 74 includes a retention feature 77 configured to be removably coupled with a complementary retention feature 78 of the tracker body 46. For example, the retention feature 77 may be external threads on an outer diameter of the plug 74 and internal threads within a counterbore 80 of the tracker body 46, or vice-versa. After the tracking element assembly 50 is assembled in a manner to be further described, the tracking element assembly 50 may be threadably secured to the tracker body 46. The tracking element assembly 50 and the tracker body 46 cooperate to define the sealed enclosure 76. Other suitable removably joining means are contemplated, for example, retaining rings, detents, defeatable interference fit, friction fit, elastic fit, and the like. It is further contemplated that the retention feature 78 need not be disposed within the counterbore 80 or otherwise internal to the tracker body 46. Alternatively, the retention feature 78 may be external to the tracker body 46. For example, a cap may be provided to secure the plug 74, or the plug 74 may include a cap that is secured to the external retention feature. In another implementation, the opening 64 and the counterbore 80 need not be coaxial in which the tracker element assembly 50 is directed into the counterbore 80 from the lower surface 62 of the tracker body 46. Rather, the tracker body 46 may define a side slot configured to slidably receive the tracker element assembly 50 whose dimensions may be modified to achieve the same.

In an alternative implementation, the tracking element assembly 50 may be fixedly secured to the tracker body 46. In other words, the tracking element assembly 50 is assembled, and the plug 74 and the tracker body 46 are permanently joined to one another through spin welding or another suitable joining process. With the sealed enclosure 76 preserving or extending the wavelength-reflecting qualities of the tracking element 70, the longer operational lifespan may justify making the tracker 44 discardable after a durable number of duty and sterilization cycles. In other words, once the sealed interfaces begin to become compromised, the entire tracker 44—including the tracker body 46 and the tracking element assembly 50—may simply be discarded.

FIG. 4 illustrates the upper surface 60 of the tracker body 46 defining the opening 64, and the lower surface 62 of the tracker body 46 defining the counterbore 80 in fluid communication with the opening 64. The opening 64 may have a diameter less than a diameter of the counterbore 80. The opening 64 and the counterbore 80 may be separated by a lip 82 of the tracker body 46. The lip 82 may include the upper surface 60 such that with the lens 66 secured against the lip 82, the lens 66 is near the opening 64. In such an arrangement, light reflected by the tracking element 70 positioned just below the lens 66 is detectable by the sensor 40 at a wider field of view (angle relative to the upper surface 60). To that end, the lip 82 may include a chamfer 84 to further maximize the field of view of the tracker 44 as represented by the bolded arrow in FIG. 4.

The coaxial stacking of the subcomponents of the tracking element assembly 50 will now be described with continued reference to FIGS. 3 and 4. The plug 74 may be disc-like in construction and define a groove 86 within an upper surface 88. The sealing element 72, for example, an O-ring, is sized to be seated within the groove 86. More particularly, the sealing element 72 may be slightly thicker than a depth of the groove 86 such that, when assembled, the sealing element 72 is compressed between the lens 66 and the plug 74. The compression prevents ingress of fluid between the lens 66 and the plug 74, thereby facilitating the sealed enclosure 76. The sealing element 72 and the upper surface 88 of the plug 74 may define a platform upon which the lens 66 rests during assembly of the tracking element assembly 50.

The plug 74 may further define a cavity 90 located radially inwardly from the groove 86. In other words, an annular barrier 92 may separate the groove 86 and the cavity 90 that are coaxial with one another. A depth of the cavity 90 is sized to accommodate certain subcomponents of the tracking element assembly 50, namely the masking spacer 68 and the tracking element 70, and a base surface 94 of the plug 74 is configured to support subcomponents of the aforementioned subcomponents. The tracking element 70 rests upon the base surface 94, and the masking spacer 68 rests upon the tracking element 70. The masking spacer 68, for example, a ring washer, is sized to a gap between the tracking element 70 and the lens 66 so as to prevent movement of the tracking element 70 within the sealed enclosure 76. In implementations in which the tracker 44 is an optical tracker, the masking spacer 68 defines an aperture 96 and is configured to create an accurate area on the reflective surface of the tracking element 70. In other words, the masking spacer 68 covers a portion of the reflective surface of the tracking element 70, and the remaining portion of the reflective surface that is visible through the aperture 96 is known with precision. Further, the masking spacer is generally thin in construction so as to prevent shadowing the reflective surface at angles off normal. Further, outer diameters of each of the masking spacer 68 and the tracking element 70 may be sized to slightly less than an inner diameter of the cavity 90. As best shown in FIG. 4, the sealed enclosure 76 may be bounded from below by the base surface 94, from above by a lower side of the lens 66, and from the sides by the annular barrier 92. The plug 74 is at least partially disposed in the counterbore 80, and the tracking element 70 is disposed in the sealed enclosure 76. It is understood that the tracking element 70, whether as a discrete component or as a coating on the lower surface of the lens 66, may be positioned at any location in the component stack-up between the upper surface of the lens 66 and the plug 74.

The plug 74 may further include a plug body 98, and a shoulder 100 extending radially outwardly from the plug body 98. With continued reference to FIG. 4, the plug body 98 includes the retention feature 77 at a first outer diameter, and the shoulder 100 may be at a second outer diameter greater than the first outer diameter. The counterbore 80 may complementarily include a widened portion 102 having an inner diameter greater than the inner diameter of the retention features 78 of the tracker body 46. The shoulder 100 is configured to be positioned in sealing engagement with the widened portion 102 of the counterbore 80 when the plug 74 is coupled to the tracker body 46. The sealing engagement between the shoulder 100 and the tracker body 46 is configured to accurately locate the plug 74 within the tracker body 46. The sealing engagement may also further prevent ingress of fluid within the subcomponents of the tracking element assembly 50, thereby further facilitating the sealed enclosure 76.

As mentioned, the tracking element assembly 50 and its subcomponents facilitate intuitive assembly of the tracker 44. A method of assembling the tracker 44 may include disposing the sealing element 72 within the groove 86 of the plug 74. The tracking element 70 may be disposed within the cavity 90 of the plug 74, and the masking spacer 68 may be disposed within the cavity 90 to rest on the tracking element 70. The steps of disposing the tracking element 70 and the masking spacer 68 may be performed before or after the step of disposing the sealing element 72 within the groove 86. The lens 66 is disposed on the platform defined by the sealing element 72 and the upper surface 88 of the plug 74. The tracking element assembly 50 may then be supported with one hand of the user, and the other hand of the user may support the tracker body 46 in the orientations generally shown in FIG. 3. The tracking element assembly 50 is moved towards the lower surface 62 of the tracker body 46 to be at least partially positioned within the counterbore 80. The complementary retention features 77, 78 engage one another, and the plug 74 is rotated to further advance the tracking element assembly 50 into the counterbore 80. The tracking element assembly 50 may be considered fully installed once the lens 66 is in abutment with the lip 82, and further in sealing engagement with the same owing to the resilient forces of the sealing element 72 under compression. The tracking element assembly 50 may further be considered fully installed once the shoulder 100 is in sealing engagement with the widened portion of the counterbore 80.

The tracker 44 may be coupled to the arm or post that itself was previously secured to the patient with known techniques. The surgical procedure may follow. The sealed enclosure 76 maintains the sterility of the tracking element 70 (and the masking spacer 68 and other internal features of the subcomponents). Following the conclusion of the surgical procedure, the tracker 44 may be decoupled from the arm or post. Without requiring further manipulation of the tracker 44, the tracker 44 may be autoclaved to sterilize all exposed subcomponents and their geometries. The sealed enclosure 76 prevents ingress of the pressurized steam, thereby preserving the light-reflecting properties of the tracking element 70. This method may be repeated as many times as viable. Only once the sealed interfaces begin to become compromised (or after a predetermined number of uses) may it be appropriate to replace the tracking element 70 and/or the sealing element 72, and doing so is intuitive and follows the aforementioned method in reverse. In the alternative implementation previously introduced in which the tracking element assembly 50 and the tracker body 46 are permanently joined, the tracker 44 may be discarded once the sealed interfaces begin to become compromised or after the predetermined number of uses.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described. In one implementation, the lens 66 may include features configured to be tracked by the sensors 60 such that the tracker 44 may not include a discrete tracking element 70. For example, the lens 66 may include an upper surface configured to be positioned against the lip 82, and a lower surface opposite the upper surface. The upper surface may be transparent, and a reflective coating may be disposed on the lower surface. The reflective coating is in the sealed enclosure. In other words, the upper surface and a thickness of the lens 66 prevents the fluid associated with autoclaving from coming into contact with the reflective coating. Alternatively, the lens 66 may be formed a layer of reflective material in another suitable construction.

What is claimed is:

1. A surgical tracker for tracking a surgical object with a navigation system, the surgical tracker comprising:
   a tracker body defining a counterbore and the tracker body being configured to attach to the surgical object;
   a lens positionable within the counterbore;
   a tracking element being configured to produce light signals that are detectable by the navigation system to facilitate tracking of the surgical object; and
   a plug comprising a plug body at least partially positionable within the counterbore and wherein the plug body defines a cavity that is sized to accommodate the tracking element; and
   wherein the tracking element is disposed within the cavity between the lens and the plug body; and
   wherein the plug, including the tracking element, is configured to be coupled with the tracker body to secure the lens and to define, with the lens, a sealed enclosure, wherein the tracking element is disposed within the sealed enclosure.

2. The tracker of claim 1, wherein the tracker body further comprises a retention feature disposed within the counterbore and configured to be removably coupled with a complementary retention feature of the plug.

3. The tracker of claim 1, wherein the tracker body defines an opening and the counterbore is in fluid communication with the opening, the tracker body comprising a lip separating the opening and the counterbore, wherein the plug is further configured to support the lens in abutment with the lip to seal the counterbore.

4. The tracker of claim 3, wherein the lip comprises a chamfer extending inwardly from an upper surface of the tracker body.

5. The tracker of claim 1, further comprising a masking spacer disposed within the sealed enclosure and between the lens and the tracking element, wherein the masking spacer defines an aperture through which a predefined portion of the tracking element is visible.

6. The tracker of claim 1, wherein the plug further comprises a shoulder extending radially outwardly from the plug body, wherein the shoulder is configured to be positioned in sealing engagement with a widened portion of the counterbore.

7. The tracker of claim 1, wherein the plug body defines a groove, the tracker further comprising a sealing element disposed within the groove.

8. The tracker of claim 1, wherein the tracking element is a coating disposed on a lower surface of the lens or an upper surface of the plug.

* * * * *